(12) United States Patent
Kawamura

(10) Patent No.: US 6,750,063 B1
(45) Date of Patent: Jun. 15, 2004

(54) METHOD FOR MEASURING CONCENTRATION OF SOLUTION AND APPARATUS FOR MEASURING CONCENTRATION OF SOLUTION

(75) Inventor: Tatsurou Kawamura, Kyotanabe (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 404 days.

(21) Appl. No.: 09/697,121

(22) Filed: Oct. 27, 2000

(30) Foreign Application Priority Data

Oct. 28, 1999 (JP) ............................................ 11-307217

(51) Int. Cl.⁷ ............................................ G01N 21/00
(52) U.S. Cl. ........................ 436/164; 436/86; 436/87; 436/34; 436/10; 436/173; 436/166; 436/169; 436/172
(58) Field of Search ................... 422/55, 56, 68.1, 422/73, 82.05; 436/164, 15, 19, 34, 165, 166, 169, 174

(56) References Cited

U.S. PATENT DOCUMENTS

| | | | |
|---|---|---|---|
| 4,090,919 A | | 5/1978 | Chibata et al. |
| 4,201,471 A | | 5/1980 | Pitt et al. |
| 4,203,724 A | * | 5/1980 | Sawai et al. .................. 436/519 |
| 4,485,176 A | * | 11/1984 | Bollin et al. .................. 436/86 |
| 4,684,252 A | | 8/1987 | Makiguchi et al. |
| 4,766,080 A | * | 8/1988 | Fleming ...................... 436/74 |
| 5,100,805 A | | 3/1992 | Ziege et al. |
| 5,104,527 A | | 4/1992 | Clinkenbeard |
| 5,178,831 A | * | 1/1993 | Sakota et al. .................. 422/56 |
| 5,212,099 A | | 5/1993 | Marcus |
| 5,264,589 A | | 11/1993 | Corey |
| 5,328,850 A | | 7/1994 | Corey |
| 5,478,748 A | * | 12/1995 | Akins et al. .................. 436/86 |
| 5,543,018 A | | 8/1996 | Stevens et al. |
| 5,922,609 A | | 7/1999 | Kellner |
| 6,036,922 A | | 3/2000 | Kawamura et al. |
| 6,297,057 B1 | | 10/2001 | Kawamura et al. |

FOREIGN PATENT DOCUMENTS

| | | | | |
|---|---|---|---|---|
| EP | 0751388 A2 | * | 2/1997 | .......... G01N/21/64 |
| EP | 0805352 A1 | | 11/1997 | |
| EP | 0845673 A2 | | 6/1998 | |
| GB | 755 900 | | 8/1956 | |
| GB | 1600139 | | 10/1981 | |
| JP | 58 209946 | | 12/1983 | |
| JP | 07 138119 | | 5/1995 | |
| JP | 9-145605 | | 6/1997 | |
| JP | 11133022 | * | 5/1999 | .......... G01N/33/493 |

* cited by examiner

*Primary Examiner*—Jill Warden
*Assistant Examiner*—Sam P. Siefke
(74) *Attorney, Agent, or Firm*—McDermott, Will & Emery

(57) ABSTRACT

An object of the present invention is provide a means capable of enlarging the measurable concentration range of a specific component in a solution to be detected, and further measuring a precise solution concentration with ease even when there occur inhibitors such as contamination of a sample cell, turbidity of the solution to be detected, and suspending particles. For achieving this object, the transmitted light intensities and/or the scattered light intensities of the solution to be detected before and after mixing a reagent for changing the optical characteristics of the solution to be detected attributed to the specific component are measured to obtain the concentration of the specific component in the solution to be detected from these measured values. Further, while obtaining the protein concentration by the foregoing method, the optical rotation of the solution to be detected is measured before the mixing of the reagent, thereby to determine the concentrations of the protein and other optical active substances than the protein.

9 Claims, 8 Drawing Sheets

METHOD FOR MEASURING CONCENTRATION OF SOLUTION AND APPARATUS FOR MEASURING CONCENTRATION OF SOLUTION

BACKGROUND OF THE INVENTION

The present invention relates to a method and an apparatus for measuring the concentration of a solute, for example, a concentration of protein and a concentration of an optical active substance dissolved in a solution to be detected.

Examples of a conventional solution concentration measuring apparatus include a spectroscope and a liquid chromatography. Whereas, as a urinalysis apparatus, there has been an apparatus whereby a test paper impregnated with a reagent or the like is dipped in a urine, and a color reaction thereof is observed by means of a spectroscope or the like to detect the components of the urine.

The test papers herein used are prepared according to the kind of respective inspection items such as glucose and protein.

However, with the forgoing method, there has presented a problem of an enlargement in size of the apparatus. Further, there has also presented another problem as follows; The concentration range measurable is restricted, so that a solution to be detected having a concentration beyond the restricted range is required to be diluted for a test, resulting in a complicated process. Still further, there have been some cases where accurate measurement results cannot be obtained under the influence of the turbidity of the solution to be detected itself, and the contamination of an optical window. Moreover, there has been a still further problem that the presence of various particles, bubbles and the like suspending in the solution to be detected within an optical path for a light, which is used for the measurement, causes a malfunction.

It is therefore an object of the present invention to provide an apparatus for measuring concentration of solution with high reliability, compactness in size, and easy maintenance and control thereof, and a measuring method enabling the apparatus design thereof, thereby solving the foregoing problems. Further, it is another object of the present invention to provide a means enabling easy and high precision urinalysis.

BRIEF SUMMARY OF THE INVENTION

For solving the foregoing problems, the present invention provides a method for measuring a concentration of specific component in a solution to be detected, the method comprising the steps of: measuring a transmitted light intensities and/or a scattered light intensities of the solution to be detected before and after being mixed with a reagent for changing the optical characteristics of the solution to be detected, attributed to the specific component; and determining the concentration of the specific component in the solution to be detected based on these measured values.

In this case, it is effective that the transmitted light intensities and the scattered light intensities are measured, and the concentration of the specific component in the solution to be detected in a low concentration region is determined from the measured values of the scattered light intensities before and after the mixing of the reagent, and the concentration of the specific component in the solution to be detected in a high concentration region is determined from the measured values of the transmitted light intensities before and after the mixing of the reagent.

Further, in this case, it is effective that the measured values of the transmitted light intensities before and after the mixing of the reagent are compared with the measured values of the scattered light intensities before and after the mixing of the reagent, thereby to detect the occurrence or non-occurrence of a false measurement due to particles suspending in the solution to be detected.

Further, it is effective that at least one of the transmitted light intensities and the scattered light intensities before and after the mixing of the reagent is measured under the same condition for a standard solution with a known concentration and the solution to be detected, and the measured values of the solution to be detected are corrected by the measured values of the standard solution to determine the concentration of the specific component in the solution to be detected.

It is effective that the standard solution is water not containing the specific component.

Further, the present invention also provides a method for measuring a concentration of solution, comprising the steps of: determining a protein concentration of the solution to be detected with the above-described method for measuring a concentration of solution; determining a total optical active substance concentration in the solution to be detected by measuring an optical rotation of the solution to be detected before the mixing of the reagent; and then determining a concentration of an optical active substance other than the protein from the protein concentration and the optical active substance concentration.

Further, the present invention also provides an apparatus for measuring a concentration of solution, comprising a light source for irradiating a solution to be detected with light; a sample cell for holding the solution to be detected such that the light transmits through the solution to be detected; a photosensor 1 for detecting the light transmitted through the solution to be detected and/or a photosensor 2 for detecting the scattered light generated when the light has propagated through the inside of the solution to be detected; a mixer for mixing a reagent, which changes the optical characteristics of only a specific component in the solution to be detected, into the solution to be detected; and a computer for controlling the mixer to analyze an output signal from the photosensor, wherein a concentration of a specific component in the solution to be detected is determined from the measured values of output signals from the photosensor 1 and/or 2 before and after the mixing of the reagent.

Still further, the present invention also provides an apparatus for measuring a concentration of solution, comprising: a monochromatic light source for projecting a substantially parallel light; a polarizer for transmitting only a polarization component in a specific direction out of the substantially parallel light, a sample cell for holding a solution to be detected such that the light transmitted through the polarizer transmits therethrough; a means for applying a magnetic field on the solution to be detected; a magnetic field control means for controlling the magnetic field; a magnetic field modulation means for vibration-modulating the magnetic field in controlling the magnetic field; an analyzer for transmitting only a polarization component in a specific direction out of the light transmitted through the solution to be detected; a photosensor for detecting the light transmitted through the analyzer; a lock-in amplifier for performing a phase sensitive detection on an output signal from the photosensor by using a vibration modulation signal from the magnetic field modulation means as a reference signal; a means for calculating the optical rotation of the solution to be detected based on the vibration control signal from the magnetic field control means and the output signal from the lock-in amplifier, and converting it into the concentration of an optical active substance; a mixing instrument for mixing into the solution to be detected, a reagent for changing the optical characteristics of only a specific component in the solution to be detected; and a computer for controlling the mixing instrument to analyze the output signal from the photosensor, wherein a protein concentration of the solution to be detected is obtained from a measured values of the transmitted light intensities of the solution to be detected measured before and after the mixing of the reagent, or from a measured value of the output signal from the photosensor by considering the output signal from the photosensor as a signal of the transmitted light, and the protein concentration of the solution to be detected and a concentration of the optical active substance other than the protein are determined from the calculated optical rotation and the protein concentration.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
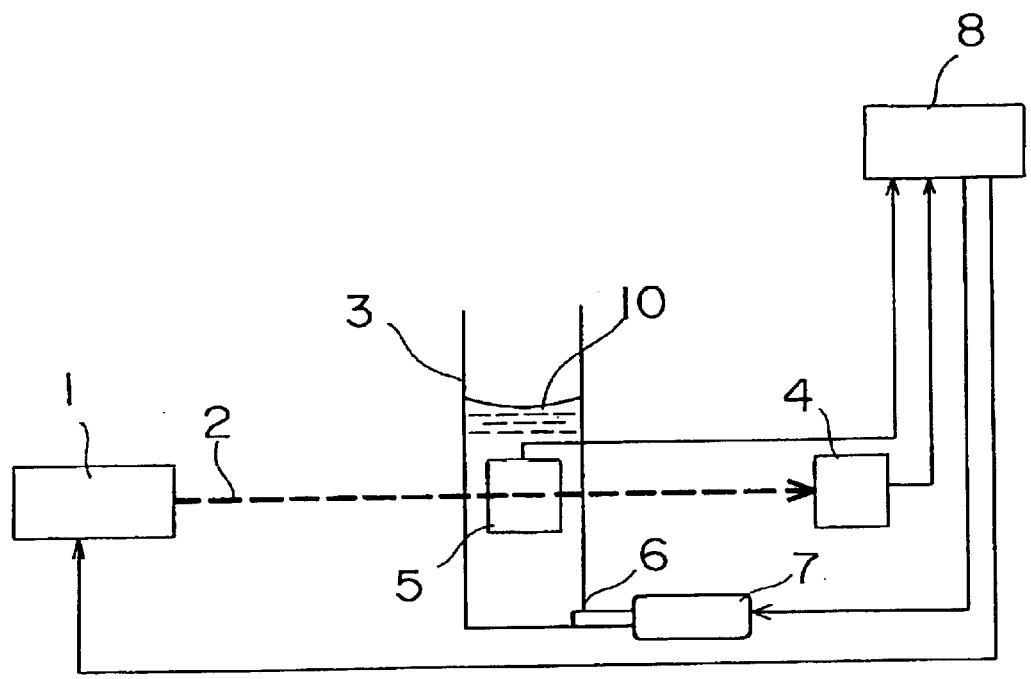
FIG. 1 is a schematic front view of a first example of an apparatus for measuring a concentration of solution in accordance with the present invention.

As described above, a method for measuring a concentration of solution of the present invention is a method for measuring a concentration of a specific component in a solution to be detected, the method comprising the steps of: measuring a transmitted light intensities and/or a scattered light intensities of the solution to be detected before and after being mixed with a reagent, which changes the optical characteristics of the solution to be detected attributed to the specific component; and determining a concentration of the specific component in the solution to be detected on these measured values.

The solution to be detected in the present invention includes a solution, which contains some suspended particles such as non-dissolved salts, dusts and bubbles.

The reagent reacts with only a specific component, which is targeted for the concentration measurement in a solution to be detected to produce discoloration and turbidity, causing the solution to be detected to undergo optical changes of such a degree as to correspond to the concentration of the specific component therein. By admixing such a reagent into the solution to be detected, it is possible to change the optical characteristics of the solution to be detected, thereby determining the concentration of the specific component. For example, when a urine is used as the solution to be detected, the reagent is mixed therewith to coagulate the protein component, thereby changing the optical characteristics of the urine. Then, from a difference in scattered light intensity between before and after the mixing of the reagent ((scattered light intensity after the mixing of the reagent)—(scattered light intensity before the mixing of the reagent)) and/or the ratio of the transmitted light intensities before and after the mixing of the reagent ((transmitted light intensity after the mixing of the reagent)/(transmitted light intensity before the mixing of the reagent)), the protein concentration in the urine can be determined.

Further, the apparatus for measuring a concentration of solution of the present invention comprises a light source for irradiating the solution to be detected with light; a sample cell for holding the solution to be detected such that the light transmits through the solution to be detected; a photosensor 1 for detecting the light transmitted through the solution to be detected and/or a photosensor 2 disposed so as to detect the scattered light generated when the light has propagated through the inside of the solution to be detected; a mixer for mixing into the solution to be detected, a reagent to change the optical characteristics of the solution to be detected, attributed to a specific component in the solution to be detected; and a computer for controlling the mixer to analyze output signals from the photosensor 1 and/or the photosensor 2, wherein the concentration of the specific component in the solution to be detected is determined from the measured values of output signals from the photosensor 1 and/or the photosensor 2 before and after the mixing of the reagent.

By measuring at least one of the transmitted light intensities and the scattered light intensities before and after the mixing of the reagent by the aforesaid method for measuring a concentration of solution or apparatus in accordance with the present-invention, it is possible to determine the concentration of the specific component in the solution to be detected. Further, the following advantages are added by measuring both of the transmitted light intensities and the scattered light intensities.

First, by determining the concentration of the specific component in the solution to be detected in a low concentration region from the measured values of the scattered light intensities before and after the mixing of the reagent, while determining the concentration of the specific component in the solution to be detected in a high concentration region from the measured values of the transmitted light intensities before and after the mixing of the reagent, the concentration of the specific component can be determined with high precision for a solution to be detected in a wider concentration region. Incidentally, the wording "high concentration" and "low concentrations" referred to in this invention will be described below.

Further, by checking the measured values of the transmitted light intensities before and after the mixing of the reagent with the measured values of the scattered light intensities before and after the mixing of the reagent, it is possible to detect the occurrence or non-occurrence of a false measurement due to suspending particles such as bubbles, various undissolved salts, dusts and dirt in the solution to be detected, thereby preventing a false measurement and a false operation of the apparatus.

Further, the transmitted light intensities before and after the mixing of the reagent and/or the scattered light intensities before and after the mixing of the reagent are measured under the same condition for a standard solution with a known concentration and the solution to be detected, and the measured values of the solution to be detected are corrected by the measured values of the standard solution to determine the concentration of the specific component in the solution to be detected. Consequently, the influences of a reduced transmittance of the optical window and the like are eliminated, and a higher precision measurement becomes possible. In this case, water not containing the specific component can be used as the standard solution.

Further, in the present invention, the optical rotation of the solution to be detected is measured before the mixing of the reagent, as well as the protein concentration of the solution to be detected is determined by any method for measuring a concentration of solution in accordance with the present invention. Thus, it is possible to determine the protein concentration and the concentration of the optical active substance other than the protein from the protein concentration and the optical rotation. For measuring the concentrations of the protein, and the optical active substance other than the protein in the solution to be detected with this method, the following apparatus can be used.

Namely, there can be used an apparatus which comprises: a monochromatic light source for projecting a substantially parallel light; a polarizer for transmitting only a polarization component in a specific direction out of the substantially parallel light; a sample cell for holding a solution to be detected such that the light transmitted through the polarizer transmits therethrough; a means for applying a magnetic field on the solution to be detected: a magnetic field control means for controlling the magnetic field; a magnetic field modulation means for vibration-modulating the magnetic field in controlling the magnetic field; an analyzer for transmitting only a polarization component in a specific direction out of the light transmitted through the solution to be detected; a photosensor for detecting the light transmitted through the analyzer; a lock-in amplifier for performing a phase sensitive detection on an output signal from the photosensor by using a vibration modulation signal from the magnetic field modulation means as a reference signal; a means for calculating the optical rotation of the solution to be detected based on the vibration control signal from the magnetic field control means and the output signal from the lock-in amplifier, and converting it into the concentration of an optical active substance; a mixer for mixing into the solution to be detected, a reagent for changing the optical characteristics of only a specific component in the solution to be detected; and a computer for controlling the mixer to analyze the output signal from the photosensor.

From the measured values of the transmitted light intensities before and after the mixing of the reagent, the protein concentration of the solution to be detected is determined. Whereas, from the calculated optical rotation and the protein concentration, the protein concentration and the concentration of an optical active substance other than the protein in the solution to be detected are determined. In this case, it is possible to measure the protein concentration of the solution to be detected from the measured value of the output signal from the photosensor by employing the output signal from the photosensor as the signal of the transmitted light.

Moreover, by further imparting a means for modulating the substantially parallel light to the aforesaid apparatus, upon mixing the reagent into the solution to be detected, and measuring the output signal from the photosensor, the output signal from the photosensor is subjected to a phase sensitive detection by taking the reference signal of the lock-in amplifier as the modulation signal of the substantially parallel light. Then, the output signal from the lock-in amplifier is considered as the signal of the transmitted light. Thus, it is also possible to measure the protein concentration of the solution to be detected from the measured values of the output signals from the lock-in amplifier before and after the mixing of the reagent, and determine the protein concentration and the concentration of an optical active substance other than the protein in the solution to be detected from the optical rotation and the protein concentration.

With the method for measuring a concentration of solution or the apparatus for measuring a concentration of solution in accordance with the present invention, it is possible to determine the concentration of a specific component contained in a solution to be detected, including a body fluid such as notably a urine, cerebrospinal fluid, blood serum, blood plasma or saliva, a food product such as a dairy product, alcohol or vinegar, an industrial liquid such as a culture solution, or an artificial dialysis solution or a liquid waste thereof. As the specific component (substance) targeted for the concentration measurement in the solution to be detected, mention may be made of various proteins such as a hormone and an enzyme, a lipid such as cholesterol, a virus, a bacteria, and the like. Further, as the reagent used for determining the concentrations of these specific components, there can be used an acid solution of trichloroacetic acid, sulfosalicylic acid or the like, an antibody solution, or the like.

Further, with the method for measuring a concentration of solution or the apparatus for measuring a concentration of solution in accordance with the present invention, the measurable concentration range of the solution to be detected can be enlarged to measure the precise concentration of the specific component such as the protein in the solution to be detected. Still further, by admixing the reagent to measure the protein concentration after measuring the optical rotation of the solution to be detected, it is possible to determine the concentration of the protein and the concentration of the optical active substance other than the protein, such as glucose at the same time. These indicate that the method for measuring a concentration of solution or the apparatus for measuring a concentration of solution in accordance with the present invention is particularly useful when the urine protein concentration and the urine sugar value are detected by using a urine as the solution to be detected, and it can enhance the reliability and the precision of the test, and largely simplify the test process.

Below, embodiments of the present invention will be described in details by way of concrete examples.

Embodiment 1

Below, a detailed description will be given to an example in which the transmitted light intensities and/or the scattered light intensities before and after mixing a reagent which changes the optical characteristics of the solution to be detected attributed to a specific component contained in the solution to be detected, into a solution to be detected are measured to obtain the concentration of the specific component in the solution to be detected from the measured values.

Figure 2:
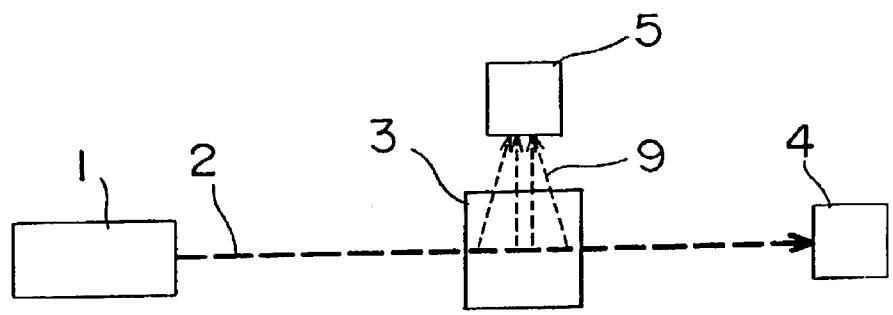
FIG. 2 is a schematic plan view of an optical system of the apparatus for measuring a concentration of solution.

FIG. 1 is a front view schematically showing a configuration of an apparatus for measuring a concentration of solution. FIG. 2 is a plan view schematically showing only the optical system of FIG. 1. In FIGS. 1 and 2, a reference numeral 1 denotes a light source composed of a semiconductor laser module, and it projects a substantially parallel light 2 with a wavelength of 780 nm, an intensity of 3.0 mW, and a beam diameter of 2.0 mm. A sample cell 3 is a rectangular parallelepiped-like container made of glass, having an opening open upwards, a base of 10×10 mm, and a height of 50 mm, wherein the sides are transparent optical windows. The sample cell 3 can irradiate a solution to be detected 10 accommodated in the inside thereof with the substantially parallel light 2. Further, a transmitted light and a scattered light 9 can be taken out therefrom to the outside. By means of a photosensor 4 for detecting the light transmitted through the solution to be detected 10, and a photosensor 5 for detecting the scattered light 9 generated when the light has propagated through the inside of the solution to be detected 10, the transmitted light and the scattered light are respectively detected. An inlet port 6 for injecting a reagent is located at the bottom of the sample cell 3. The reagent is injected in a prescribed amount into the solution to be detected in the sample cell 3 by a pipette 7 through the inlet port 6. A computer 8 controls the light source 1 and the pipette 7 to analyze output signals from the photosensors 4 and 5.

When a urine protein concentration is detected using a urine as a solution to be detected by means of the apparatus for measuring a concentration of solution, the operation thereof is as follows.

First, the solution to be detected 10 is introduced into the sample cell 3. The computer 8 operates the light source 1, while starting monitoring of the respective output signals from the photosensors 4 and 5 simultaneously therewith. Then, the computer 8 controls the pipette 7 to introduce a sulfosalicylic acid reagent (a reagent obtained by dissolving sodium sulfate in an aqueous solution of 2-hydroxy-5-sulfobenzoic acid) into the sample cell 3 through the inlet port 6. When the sulfosalicylic acid reagent is mixed into the solution to be detected, the protein component is coagulated, so that the solution to be detected 10 becomes turbid, resulting in a reduction in transmitted light intensity and an increase in scattered light intensity. The measured values of the respective output signals from the photosensors 4 and 5 before and after the mixing of the reagent are analyzed to obtain the protein concentration.

Figure 3:
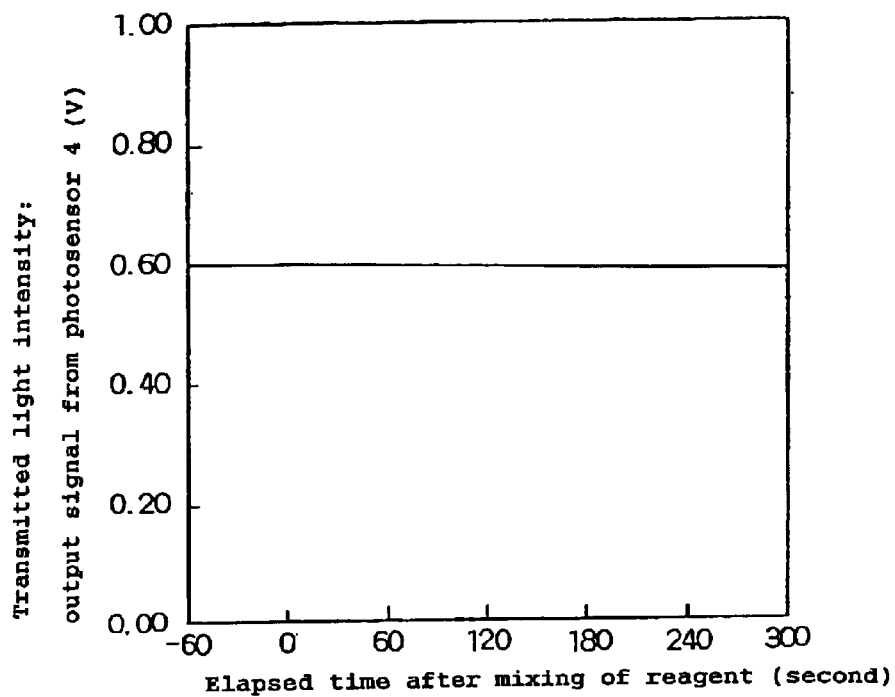
FIG. 3 is a graph showing the transmitted light intensity of a solution to be detected of the first example, determined by the apparatus for measuring a concentration of solution.
Figure 4:
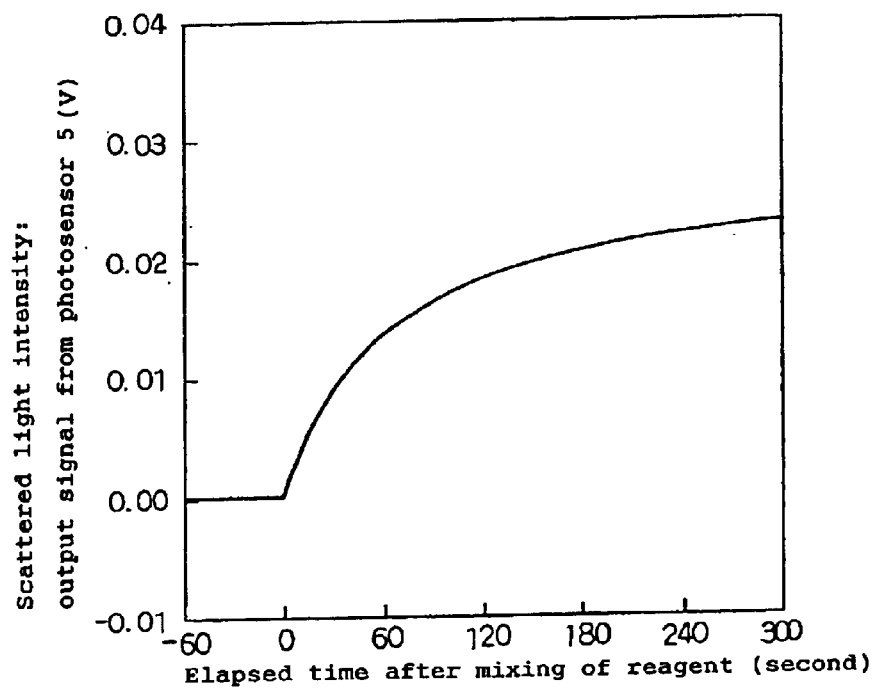
FIG. 4 is a graph showing the scattered light intensity of the solution to be detected, determined by the apparatus for measuring a concentration of solution.
Figure 5:
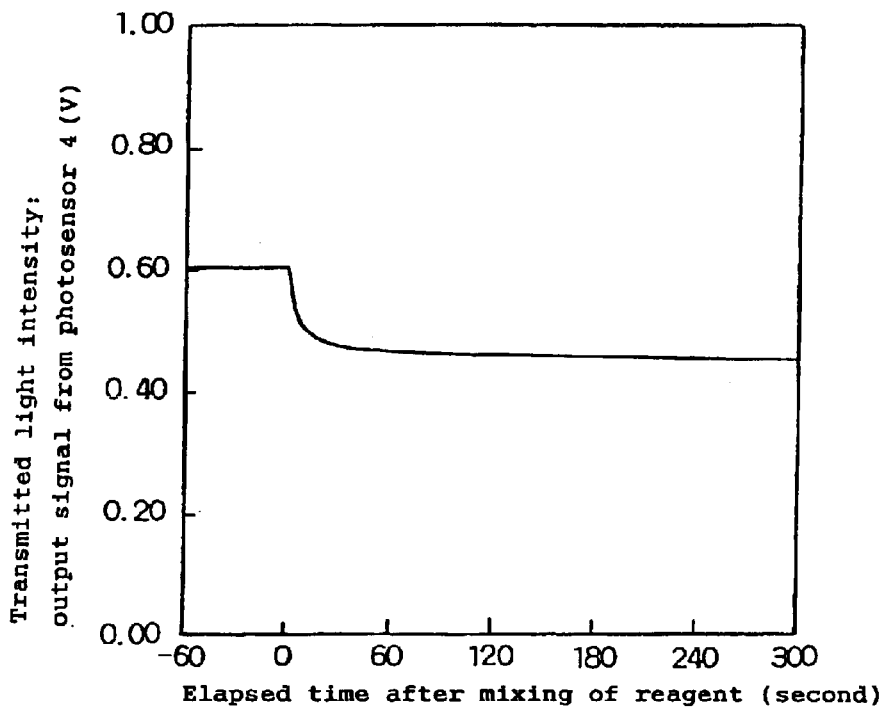
FIG. 5 is a graph showing the transmitted light intensity of a solution to be detected of a second example, determined by the apparatus for measuring a concentration of solution.
Figure 6:
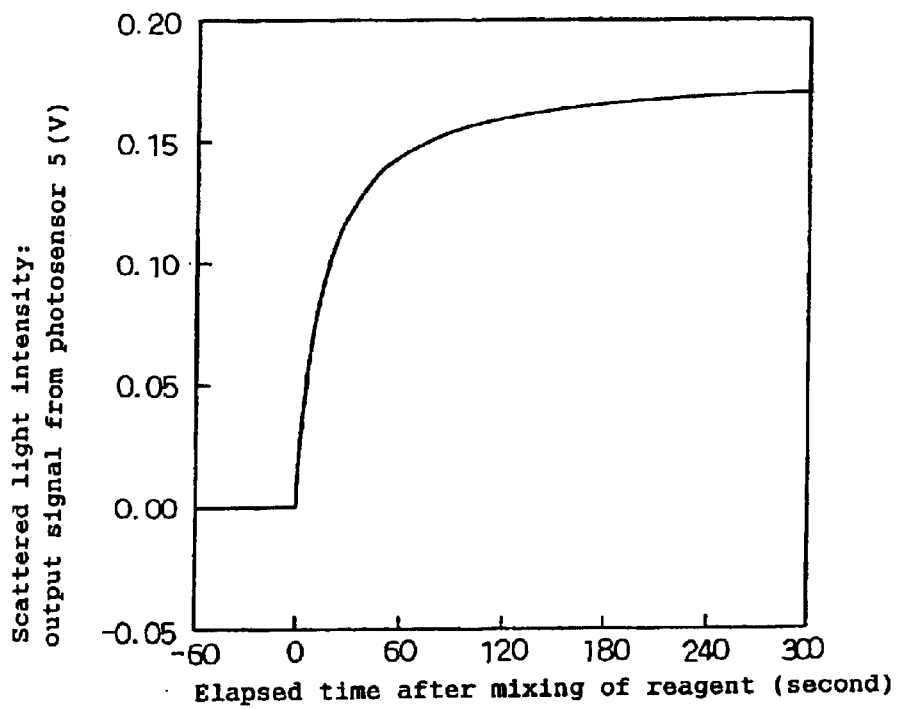
FIG. 6 is a graph showing the scattered light intensity of the solution to be detected, determined by the apparatus for measuring a concentration of solution.
Figure 7:
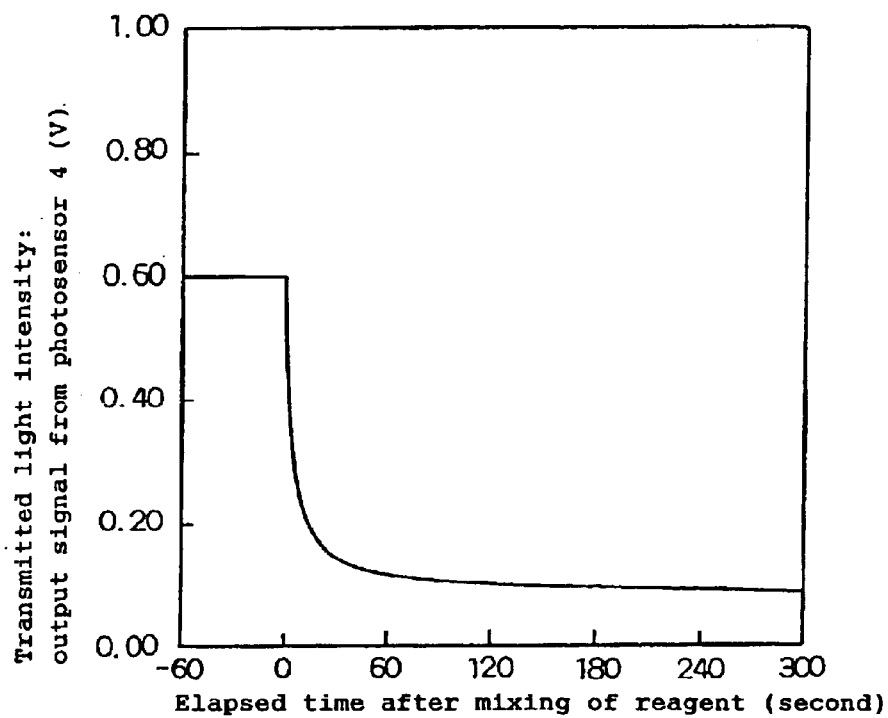
FIG. 7 is a graph showing the transmitted light intensity of a solution to be detected of a third example, determined by the apparatus for measuring a concentration of solution.
Figure 8:
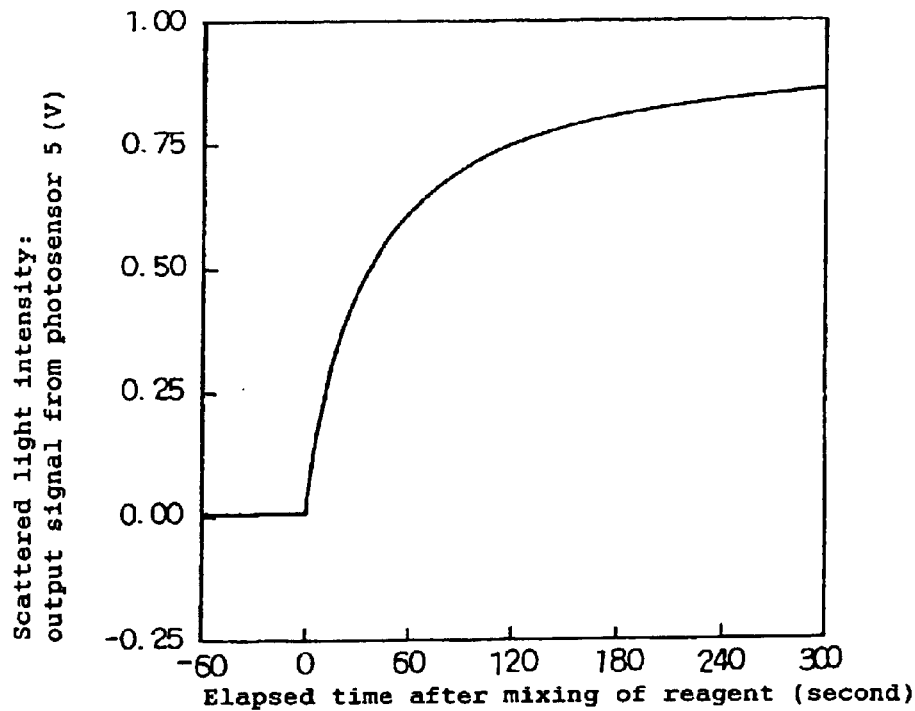
FIG. 8 is a graph showing the scattered light intensity of the solution to be detected, determined by the apparatus for measuring a concentration of solution.

The transmitted light intensity and the scattered light intensity, i.e., the respective output signals from the photosensors 4 and 5 measured by the foregoing method using the solution to be detected 10 with a protein concentration of 2 mg/dl, are shown in FIGS. 3 and 4, respectively. Similarly, respective output signals when a solution to be detected with a protein concentration of 15 mg/dl is used are shown in FIGS. 5 and 6, respectively. Meanwhile, respective output signals when a solution to be detected with a protein concentration of 100 mg/dl is used are shown in FIGS. 7 and 8, respectively. In FIGS. 3 to 8, the abscissa indicates the elapsed time (second) after the mixing of the reagent, while the ordinate indicates the changes in the transmitted light intensity or scattered light intensity from 60 seconds before the mixing to 300 seconds after the mixing. FIGS. 3, 5, and 7 indicate that the intensity of the transmitted light (the output signal from the photosensor 4) decreases with an increase in concentration of the protein. Whereas, FIGS. 4, 6, and 8 indicate that the intensity of the scattered light (the output signal from the photosensor 5) increases with an increase in concentration of the protein.

Figure 9:
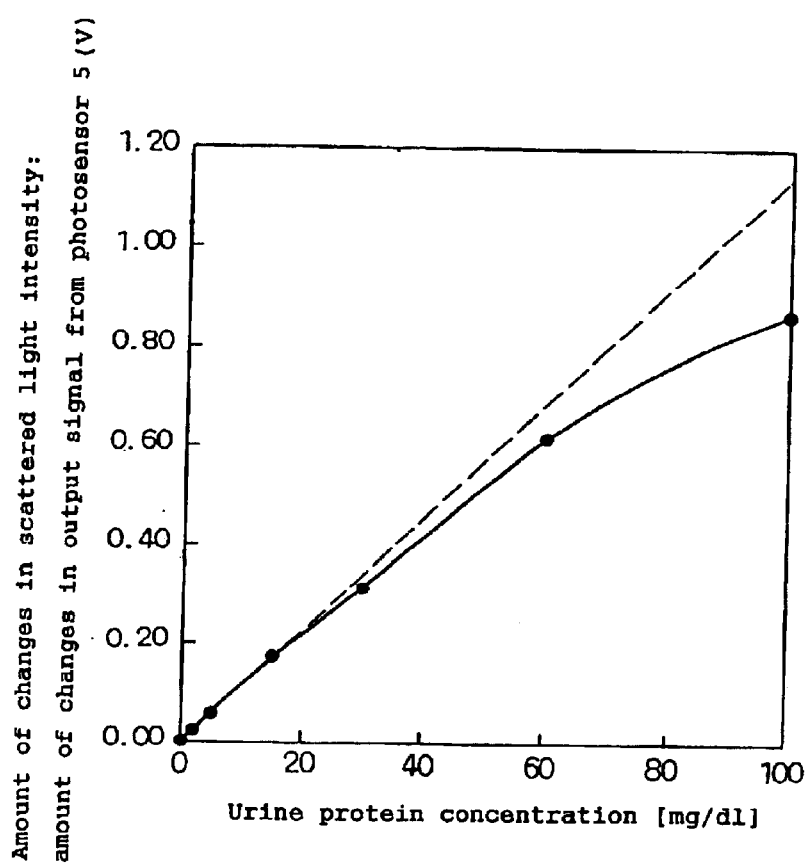
FIG. 9 is a graph showing an example of a calibration curve for determining a urine protein concentration from the scattered light intensity in accordance with the present invention.
Figure 10:
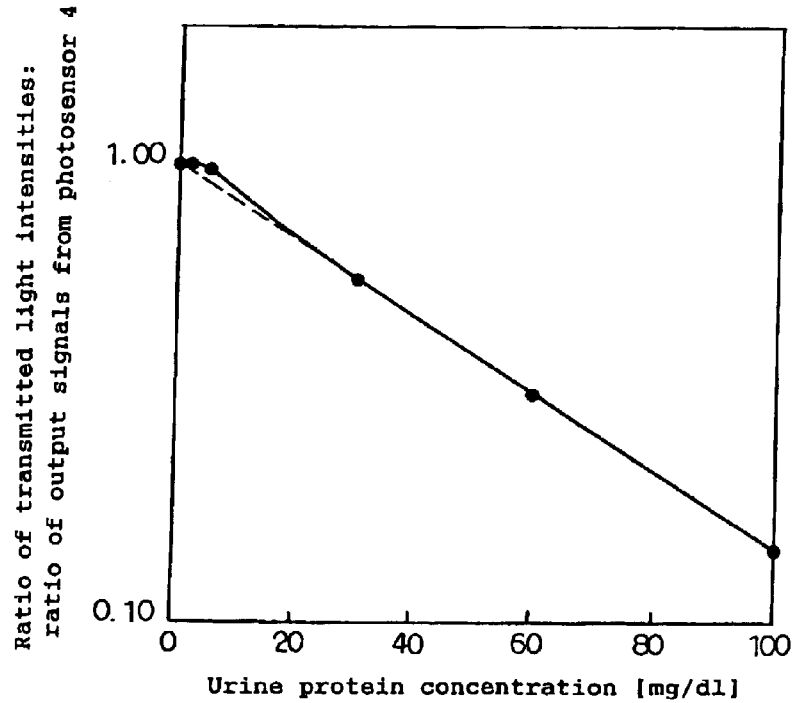
FIG. 10 is a graph showing an example of a calibration curve for determining a urine protein concentration from the transmitted light intensity in accordance with the present invention.

Such correlations between changes in scattered light intensity and changes in transmitted light intensity, and the protein concentrations are shown in FIGS. 9 and 10. In FIG. 9, a difference between the scattered light intensity after an elapse of 300 seconds from the mixing of the reagent and the scattered light intensity before the mixing ((the scattered light intensity after the mixing of the reagent)—(the scattered light intensity before the mixing of the reagent)) is plotted as ordinate. In FIG. 10, the ratio of the transmitted light intensity after an elapse of 300 seconds from the mixing to the transmitted light intensity before the mixing of the reagent ((the transmitted light intensity after the mixing of the reagent)/(the transmitted light intensity before the mixing of the reagent)) is plotted as ordinate. It is notes that the results obtained by carrying out additional measurements using urines with respective protein concentrations of 0.5, 30, and 60 mg/dl as the solutions to be detected in addition to the aforesaid solution to be detected are shown in FIGS. 9 and 10. In these cases, all the solutions subjected to the measurements have been optically as transparent as water before the mixing of the reagent, and the transmitted light intensities and the scattered light intensities thereof have been identical to those for water. Therefore, each correlation obtained therefrom of FIGS. 9 and 10 can be used as a standard calibration curve when the protein concentration in each urine is measured.

In FIG. 9, respective measured values are smoothly connected to be represented by a solid line, and the straight line connecting the measured values within the region of a protein concentration of from 0 to 15 mg/dl which shows a linear change with respect to the amount of changes in scattered light intensity (a difference in scattered light intensity between before and after the mixing of the reagent) is extended to be represented by a dotted line. Apparent from the solid line and the dotted line, the solid line and the dotted line overlap one another, and the amount of changes in scattered llght intensity is proportional to the protein concentration in the region where the protein concentration is up to about 15 mg/dl.

However, as the concentration increases more than this value, measured values gradually decrease lower than the values satisfying the proportional relationship. The reason for this is as follows. When the protein concentration is increased, so that the probability that light is scattered is increased, there is also the increased probability that light is scattered again during propagation of light from the point where the scattered light has generated to the outside of the sample cell, resulting in a reduction in probability that the scattered light reaches the photosensor 5. Therefore, when the concentration is calculated from the changes in scattered light intensity, it is possible to determine a more precise concentration in the low concentration region (about 15 mg/dl or less) where the linearity can be ensured.

In FIG. 10, the abscissa denotes the protein concentration, while the ordinate (logarithmic scale) denotes the ratio of the transmitted light intensities before and after the mixing of the reagent. Respective measured values are smoothly connected to be represented by a solid line, and the straight line connecting the measured values linearly changing within a protein concentration of 15 to 100 mg/dl is extended to be represented by a dotted line. As shown in FIG. 10, when the protein concentration is as low as 2 mg/dl or 5 mg/dl, the measured value may deviate from the dotted line. The reason for this is that, apparent from the comparison between FIGS. 3, 5, and 7, since the ratio of change is too small as compared with all the output signals, the measured value is susceptible to various noises. This indicates that, when the protein concentration is calculated from the measured values of the transmitted light intensities, the solution to be detected is more desirably falls within the high concentration region (about 15 mg/d or more) for avoiding the influences of various noises.

In the foregoing manner, by measuring the transmitted light intensities before and after the mixing of the reagent, or the scattered light intensities before and after the mixing of the reagent, it is possible to obtain the concentration of a specific component in a solution to be detected.

Further, by measuring both the intensities, the solution concentration is calculated form the measured values of the scattered light intensities for the solution to be detected within the low concentration region, while the solution concentration is calculated form the measured values of the transmitted light intensities for the solution to be detected within the high concentration region. Accordingly, the concentration range of the solution to be detected measurable with substantially high precision, i.e., dynamic range can be enlarged.

Consequently, by the present invention, the conventionally required processes such as dilution of a high concentration solution to be detected becomes unnecessary, and hence it is possible to enhance the practical effects effective for achieving the higher precision, higher efficiency, and laborsaving of the measurement and test.

Further, although the solution concentration has been obtained from the measured values of the transmitted light intensities and the scattered light intensities immediately before the mixing of the reagent and after an elapse of 300 seconds from the mixing of the reagent in this embodiment, the time difference may be appropriately set according to the characteristics of the measuring apparatus, the solution to be detected, and the reagent.

In this embodiment, assuming that the concentration in the low concentration region is about 15 mg/dl or less, and the concentration in the high concentration region is about 15 mg/dl or more, the scattered light intensities are measured in the low concentration region, the transmitted light intensities are measured in the high concentration region. Consequently, high-precision results can be obtained.

However, since the low concentration and high concentration regions in this embodiment vary depending upon various factors such as the optical path length of the sample cell 3, the propagation distance in the solution to be detected of the scattered light 9, the arrangement of the optical system and the like, they are not limited to the foregoing numerical range.

Therefore, the wording "low concentrations" herein referred to in the present invention denotes the concentration range corresponding to the portion having a linearity in the graph (FIG. 9) showing the relation between the specific component concentration of the solution to be detected and the scattered light intensity changes. Whereas, the wording high concentrations herein used denotes the concentration range corresponding to the portion having a linearity in the graph (FIG. 10) showing the relation between the specific component concentration of the solution to be detected and the transmitted light intensity ratio. These can be previously determined prior to carrying out the method in accordance with the present invention by any those skilled in the art.

If the optical path length of the transmitted light is actually elongated longer than 10 mm described above, the transmitted light intensity can be measured with high precision even in the case of a concentration of 15 mg/dl or less However, when the optical path length is elongated to such a length, the optical signal from the photosensor 4 becomes too small (about $10^{-4}$ V) in the high concentration region, and hence it becomes difficult to obtain the concentration. Further, an elongation in optical path length inevitably enlarges the entire scale of the apparatus, and such a large scale apparatus is not very preferable from the practical viewpoint.

As described above, according to the present invention, when the structure and the scale of the apparatus have a certain restriction, by utilizing both the scattered light and the transmitted light, it is possible to measure the concentration with high precision in all of the high concentration region and the low concentration region, and enlarge the dynamic range.

Embodiment 2

A detailed description will be given to an example in which the concentration of a specific component is determined by using a urine as a solution to be detected, which is made turbid by precipitation of various salts and the like, by means of the measuring apparatus in FIGS. 1 and 2.

First, a turbid urine with a protein concentration of 15 mg/dl is introduced as the solution to be detected 10 into the sample cell 3 to observe the changes in output signals from the photosensor 4 and/or the photosensor 5 before and after the mixing of the reagent in the same manner as in Embodiment 1.

Figure 11:
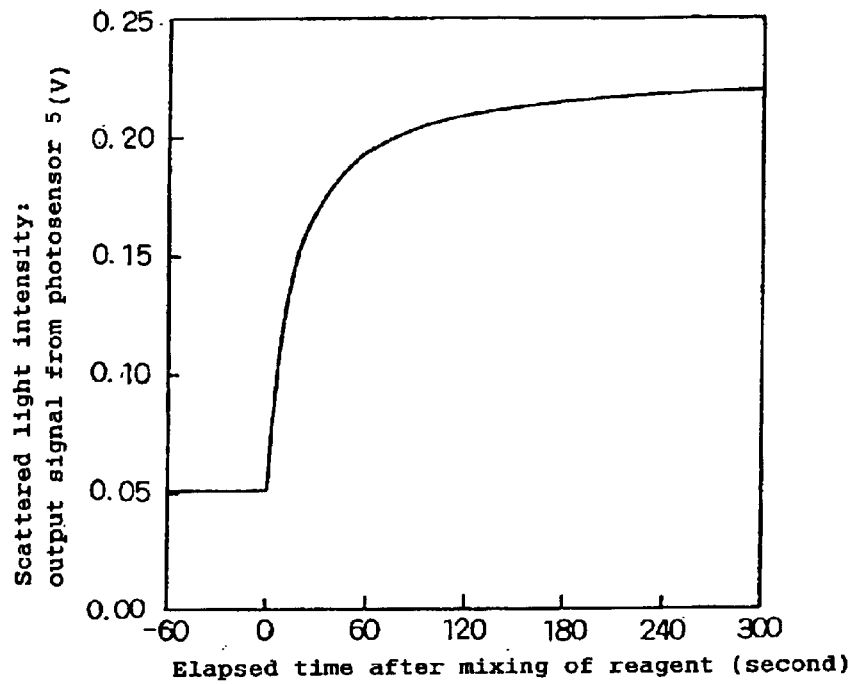
FIG. 11 is a graph showing the scattered light intensity of a suspension to be detected, determined by the apparatus for measuring a concentration of solution.
Figure 12:
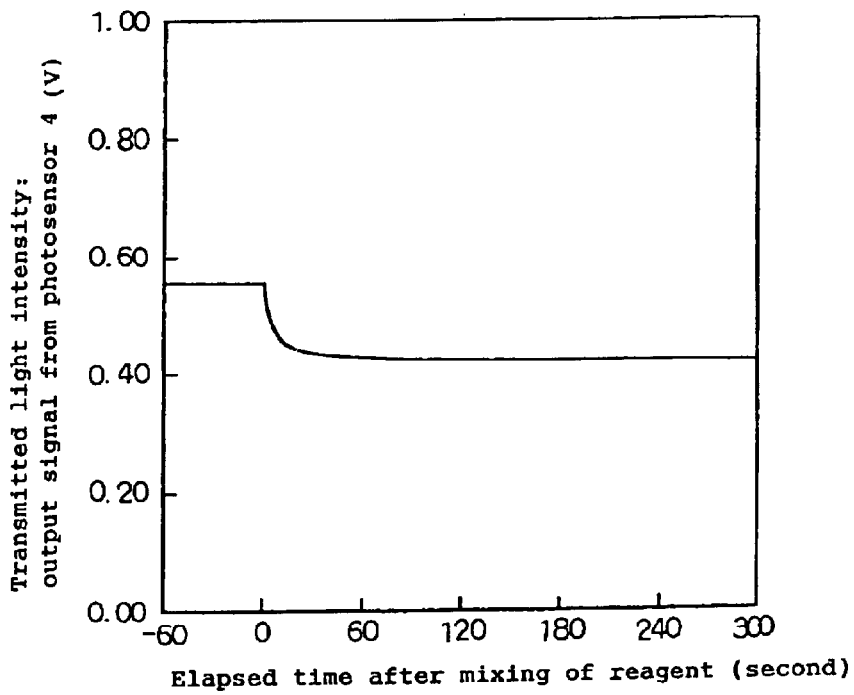
FIG. 12 is a graph showing the transmitted light intensity of a suspension to be detected, determined by the apparatus for measuring a concentration of solution.

The changes with time in output signals from the photosensors 4 and 5 before and after the mixing of the reagent are shown in FIGS. 11 and 12, respectively. These graphs represent the changes in output signals during from 60 seconds before the mixing of the reagent to 300 seconds after the mixing of the reagent as with FIGS. 3 to 8.

Apparent from FIG. 11, the output signal from the photosensor 5 (scattered light intensity) before the mixing of the reagent, i.e., during from −60 to 0 second is about 0.05 V. In the case of the turbidity-free solution to be detected as used in Embodiment 1, the output signal from the photosensor 5 before the mixing is 0.0 V. Therefore, it can be said that the difference in output signal therebetween indicates the degree of turbidity inherent in the solution to be detected of this embodiment. When the value is converted into the protein concentration by referring to FIG. 9 as a calibration curve, it corresponds to 4 to 5 mg/dl.

On the other hand, the output signal from the photosensor 5 at the time after an elapse of 300 seconds from the mixing of the reagent is 0.22 V, so that the difference from the output signal at a time point of 0 second is 0.17 V. The difference in output signals (0.17 V) is converted into the protein concentration by referring to FIG. 9 as a calibration curve to be 15 mg/dl. This concentration is identical to the known concentration previously measured. This confirms that the protein concentration of the turbid solution to be detected can be determined precisely from the difference between output signals from the photosensor 5 before and after the mixing of the reagent by using the calibration curve of FIG. 9, which is determined from the turbidity-free solution to be detected.

As described above, by calculating the solution concentration from the difference in scattered light intensity between before and after the mixing of the reagent, it is possible to determine a precise solution concentration from which influences of turbidity and the like have been eliminated.

Further, in FIG. 12, at the time point before the mixing of the reagent, i.e., from −60 to 0 second, the output signal from the photosensor 4 (transmitted light intensity) is 0.55 V. On the other hand, in the case of the turbidity-free solution to be detected as used in Embodiment 1, the output signal from the photosensor 4 before the mixing is 0.6 V. Therefore, it can be said that the difference is due to the turbidity of the solution to be detected. FIG. 12 indicates that the output signal from the photosensor 4 before the mixing of the reagent is 0.55 V, while the output signal at a time point after an elapse of 300 seconds from the mixing is 0.42 V, and the ratio thereof is 0.76. The ratio of the output signals (0.76) is converted into the protein concentration by referring to FIG. 10 as a calibration curve to be 15 mg/dl. This concentration is identical to the known concentration previously measured. This confirms that the protein concentration of the turbid solution to be detected can be determined with precision by determining the ratio of output signals from the photosensor 4 before and after the mixing of the reagent referring to FIG. 10 as a calibration curve, and converting it into the protein concentration by reference to FIG. 10 determined based on the turbidity-free solution to be detected as a calibration curve.

Further, when the protein concentration is determined from changes in transmitted light intensity, it is also possible to use a biuret reagent (a reagent obtained by dissolving potassium sodium tartrate and sodium sulfate in a sodium hydroxide solution) other than the aforesaid reagent. However, in this case, it is preferable to use a light source with a wavelength of about 540 nm. Even when a turbid solution to be detected is measured by using it, it becomes possible to determine the concentration with precision without being affected by turbidity and the like as in this embodiment.

Embodiment 3

Below, a description will be given to an example wherein both the output signals from the photosensors 4 and 5 are measured by using the measuring apparatus shown in FIGS. 1 and 2 in the same manner as in Embodiment 1, and both the measured values are compared with each other, thereby to detect the occurrence or non-occurrence of measurement obstruction due to suspending particles, bubbles, or the like.

When suspending particles or bubbles are present in the solution to be detected, and they enter the optical path of the substantially parallel light 2, the substantially parallel light 2 is highly scattered by them to obstruct the precise measurement of the transmitted light and/or scattered light intensity. In this case, the transmitted light intensity is remarkably decreased, while the scattered light intensity may remarkably decreased or increased according to the viewing angle of the photosensor 5, the position at which suspending particles or bubbles are present in the optical path, and the like.

When there is no obstruction due to the suspending particles or bubbles, as shown in FIGS. 9 and 10, there is a certain relation between the measured value of the scattered light intensity and the measured value of the transmitted light intensity. For example, when the protein concentration of the solution to be detected is 15 mg/dl, the difference in scattered light intensity between before and after the mixing of the reagent is 0.17 V, and the ratio of the transmitted light intensities before and after the mixing is 0.76. However, when the foregoing obstruction occurs, the values deviating from such a relationship are obtained as measured values.

Therefore, the occurrence or non-occurrence of the obstruction can be detected by checking whether or not the protein concentration determined from the measured values of the output signals from the photosensor 4 before and after the mixing of the reagent based on the calibration curve of FIG. 9 and the protein concentration determined from the measured values of the output signals from the photosensor 5 before and after the mixing of the reagent based on the calibration curve of FIG. 10 are identical to each other.

As described above, according to this embodiment, by measuring both the transmitted light intensities before and after the mixing of the reagent and the scattered light intensities before and after the mixing of the reagent, and checking them with each other, it is possible to detect the obstruction due to bubbles, various non-dissolved salts, and suspending particles such as dusts and dirt, thereby preventing a false measurement. Consequently, the reliability of the measurement can be improved, and the practical effect thereof is very high, thereby making it possible to achieve the higher reliability and the laborsaving of the measurement and the test.

Embodiment 4

Below, a description will be given to an example wherein when there occurs a reduction in transmittance of the optical window due to a stain, contamination or the like of the sample cell in the measuring apparatus shown in FIGS. 1 add 2, respective output signals from the photosensor 4 and/or the photosensor 5 are measured under the same conditions for both the solution to be detected and the standard solution, and the measured value of the solution to be detected is corrected by the measured value of the standard solution to determine the concentration of a specific component in the solution to be detected.

In such a case that the sample cell 3 has been used for a long time, various residual substances adhere thereto, resulting in a reduction in transmittance of each optical window. In this case, since the absolute value of the transmitted light intensity is decreased, the precision of the ratio of the transmitted light intensities between before and after the mixing of the reagent is reduced. Accordingly, the difference in scattered light intensity between before and after the mixing of the reagent is decreased. Therefore, in these cases, it is not possible to determine the solution concentration with high precision.

The influence of a reduction in transmittance of the optical window due to such long-term use can be corrected by carrying out the measurement on the solution to be detected with a known protein concentration (standard solution). For example, a measurement is previously carried out for a standard solution with a protein concentration of 15 mg/dl. In this step, when the difference in scattered light intensity between before the mixing of a sulfosalicylic acid reagent and after an elapse of 300 seconds from the mixing thereof is 0.15 V, the calibration curve of FIG. 9 obtained in Embodiment 1 is corrected in the following manner. Namely, since the aforesaid difference in scattered light intensity when the protein concentration is 15 mg/dl is 0.17 V, the solution concentration is determined by using another calibration curve obtained by multiplying the concentration obtained from the calibration curve of FIG. 9 by 0.17/0.15 for correction.

As described above, by measuring the changes in scattered light intensity between before and after the mixing of the reagent of the standard solution, and checking the measured values against a known calibration curve, it is possible to obtain another calibration curve corrected for the influence of the reduction in transmittance of the optical window. By using this, even when the optical window has a reduced transmittance, a precise concentration measurement becomes possible.

Embodiment 5

A description will be given to an example in which water containing no specific component is used as the standard solution for correcting the influence of the reduction in transmittance of the optical window described in Embodiment 4.

When the solution to be detected is water containing no specific component, since the concentration of the specific component which is allowed to react due to the mixing of the reagent to change the optical characteristics of water is zero, there arises no difference in scattered light intensity as shown in Embodiment 4. Therefore, the numerical value required for the correction cannot be calculated. Then, the transmitted light intensity with water contained in the sample cell 3 is measured. For example., when the transmitted light intensity at this step is 0.5 V, correction is carried out in the following manner. FIGS. 3, 5, and 7 indicate that the transmitted light intensity in the state where the solution is transparent before the mixing of the reagent is 0.6 V. Accordingly, by conducting such a correction that the concentration obtained from the calibration curve of FIG. 9 is multiplied by 0.6/0.5, it is possible to determine a precise concentration.

As described above, by measuring the transmitted light intensity using water as a standard solution, it is possible to correct the influence of the reduction in transmittance of the optical window. Further, when the respective manners in which the residual substances adhere to the optical windows are equal, the optical window for emitting a transmitted light and the optical window for emitting a scattered light undergo the same reduction in transmittance. Therefore, the amount of changes in scattered light intensity can be corrected from the reduction of the transmitted light intensity with respect to water.

As described above, according to this embodiment, water can be used as the standard solution, and hence the reduction in transmittance of each optical window can be corrected with ease. Especially, in a home where a protein aqueous solution is difficult to control and store, or the like, the control and storage thereof is easy, and hence the practical effect is very large.

Embodiment 6

Below, a detailed description will be given to an example in which the optical rotation of a solution to be detected is measured before the mixing of the reagent, while the transmitted light intensities of the solution to be detected are measured before and after the mixing of the reagent, thereby to determine the protein concentration and the concentration of an optical active substance other than the protein from these measured values.

Figure 13:
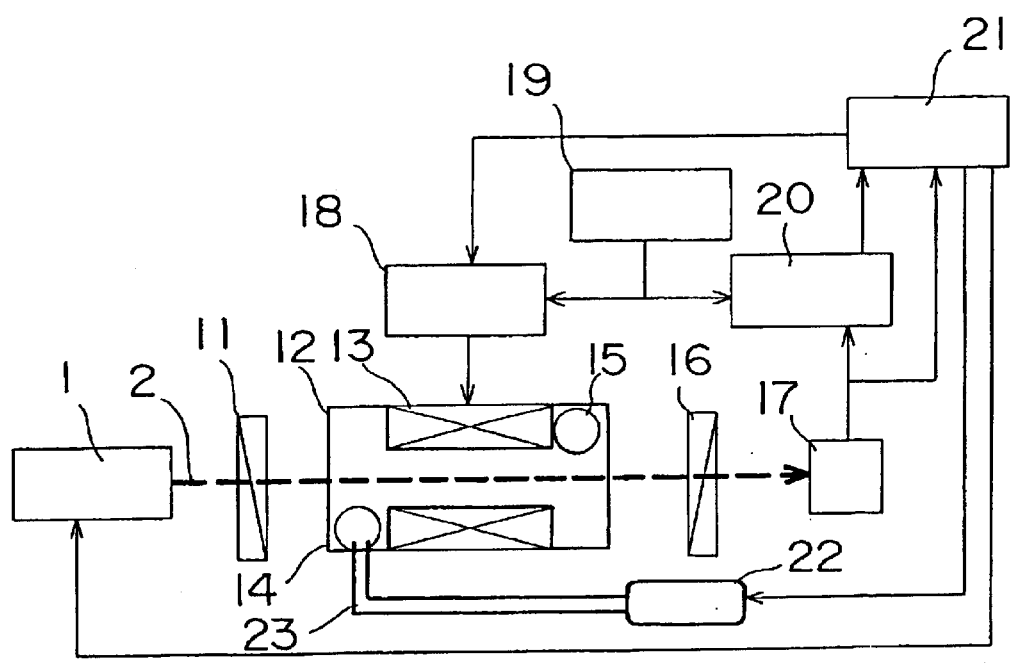
FIG. 13 is a schematic front view of a second example of an apparatus for measuring a concentration of solution in accordance with the present invention.

FIG. 13 is a schematic view of a measuring apparatus based on a measuring method of this embodiment. The substantially parallel light 2 with a wavelength of 670 nm, an intensity of 3.0 mW, and a beam diameter of 2.0 mm is projected from the light source 1 of a semiconductor laser module. A polarizer 11 transmits only a light of the polarization component parallel to the plane of a sheet of paper. A sample cell 12 for accommodating a solution to be detected is so configured that a solenoid coil 13 is wound therein so as to apply a magnetic field on the solution to be detected along the direction of propagation of the substantially parallel light 2, and it has a substantial optical path length of 10 mm. This configuration is for controlling the current to be passed through the solenoid coil 13 while modulating it by using the optical Faraday effect of the solution to be detected, thereby controlling the polarization direction of the substantially parallel light 2 while modulating it. Thus, the basic principle of the method for measuring the optical rotation by the optical Faraday effect of the solution to be detected itself is described in Japanese Laid-Open Patent Publication No.Hei 9-145605.

A reagent is mixed through an inlet port 14 into the sample cell 12, and air goes in and out through a vent hole 15. An analyzer 16 is disposed so as to transmit only a light of the polarization component perpendicular to the plane of a sheet of paper. The substantially parallel light 2 transmitted through the analyzer 16 is detected by a photosensor 17.

The electric current to be passed through the solenoid coil 13 is controlled by a coil driver 18, and a modulation signal for modulating the current to be passed through the solenoid coil 13 is supplied to the coil driver 18 by a signal generator 19. A lock-in amplifier 20 performs a phase sensitive detection on an output signal from the photosensor 17 by using the modulation signal from the solenoid coil 13 as a reference signal. When the optical rotation of the solution to be detected is measured, a control current signal is supplied by a computer 21 to the coil driver 18 so that the output signal from the lock-in amplifier 20 becomes zero.

In the case of this embodiment, a modulation current with an amplitude of 0.001 ampere and a frequency of 1.3 kHz is passed through the solenoid coil 13. Consequently, the control current signal when the output signal from the lock-in amplifier 20 becomes zero is found to calculate the optical rotation. Herein, there has been adopted the following method. Namely, the optical rotation is determined by the control current signal, which provides such a magnetic field that the optical rotation generated by an optical active substance such as a protein or a glucose in the solution to be detected is identical to the angle of rotation of the polarization direction due to the Faraday effect of a solvent solution for the solution to be detected by application of a magnetic field.

Then, a pipette 22 injects a prescribed amount of a reagent from the inlet port 14 through a tube 23 into the solution to be detected in the sample cell 12. The computer 21 controls the light source 1 and the pipette 22, and analyzes the output signal from the photosensor 17.

When the glucose concentration (urine sugar value) and the urine protein concentration are detected using a urine as the solution to be detected, the operation thereof is as follows.

First, the solution to be detected is introduced in the sample cell 12. The light source 1 and the coil driver 18 are operated by the computer 21 to measure the optical rotation of the solution to be detected.

Then, with the computer 21, the operation of the coil driver 18 is stopped, while the monitoring of the optical signal from the photosensor 17 is initiated simultaneously therewith. Then, the pipette 22 is controlled by the computer 21 to mix the sulfosalicylic acid reagent through the inlet port 14 into the solution to be detected in the sample cell 12. By assuming that the changes in output signal from the photosensor 17 before and after the mixing are the changes in transmitted light intensity, a calibration curve corresponding to that of FIG. 10 is formed from the ratio of the analyzed transmitted light intensities before and after the mixing of the reagent by the same method as in Embodiment 1.

As an example of the foregoing measurement, the measured value of the optical rotation when a urine with a urine sugar value of 100 mg/dl and a urine protein concentration of 15 g/dl was used as the solution to be detected was found to be 0.0034°. The specific rotatory power of glucose at this wavelength (670 nm) is 40° deg/cm·dl/kg. Accordingly, if it is assumed that the optical rotation measured totally occurs due to glucose, the glucose concentration, i.e., the urine sugar value is calculated to be 85 mg/dl. On the other hand, the protein concentration determined from the ratio of the transmitted light intensities was 15 mg/dl. Accordingly, since the specific rotatory power of the protein is −40° deg/cm·dl/kg, the optical rotation occurred due to the protein is calculated to be −0.0006°. Therefore, the true optical rotation occurred due to glucose is 0.0040° which is obtained by subtracting −0.0006° from 0.0034° described above, and the glucose concentration corresponding to this optical rotation is calculated to be 100 mg/dl.

From the foregoing description, in accordance with this embodiment, it could be confirmed that the urine sugar value and the urine protein concentration can be determined with precision simultaneously by measuring the optical rotation of the solution to be detected before the mixing of the reagent and the ratio of the transmitted light intensities before and after the mixing of the reagent. Incidentally, the measurement of the protein concentration (15 mg/dl) was carried out by taking the output signal from the photosensor 17 as the signal indicative of the transmitted light intensity to measure the values before and after the mixing of the reagent, and checking them against the calibration curve previously formed.

As described above, in accordance with this embodiment, since the protein concentration and the concentration of glucose as an optical active substance other than the protein can be measured at the same time, the practical utility thereof is particularly high when a urine is used as the solution to be detected. The reason for this will be described below.

When the urine protein concentration is normal, since glucose is predominant as the optical active substance in a urine, the urine sugar value can be roughly detected by measuring the optical rotation of the urine. However, a more precise urinalysis can be carried out by determining the urine protein concentration with other measuring method than the measurement of the optical rotation. The reason for this is as follows. Since the protein is also the optical active substance as glucose, the total optical rotation obtained by adding the optical rotation occurred due to glucose with the optical rotation occurred due to protein is measured as the optical rotation of the urine. Then, as in this embodiment, the protein concentration is obtained from the changes in optical properties before and after the mixing of the reagent as described above together with the measurement of the optical rotation. By correcting the measured results of the optical rotation based on this concentration, it is possible to determine the urine sugar value and the urine protein value with precision.

Incidentally, if the reagent is mixed therein prior to the measurement of the optical rotation, the protein component undergoes coagulation or coloration. Accordingly, light may not transmit through the inside of the solution to be detected, or the protein may be modified to change the optical rotation. Thus, the urine sugar value and the urine protein concentration cannot be measured with precision.

Embodiment 7

A detailed description will be given to another example wherein the protein concentration and the concentration of an optical active substance other than the protein in the solution to be detected are measured at the same time.

Figure 14:
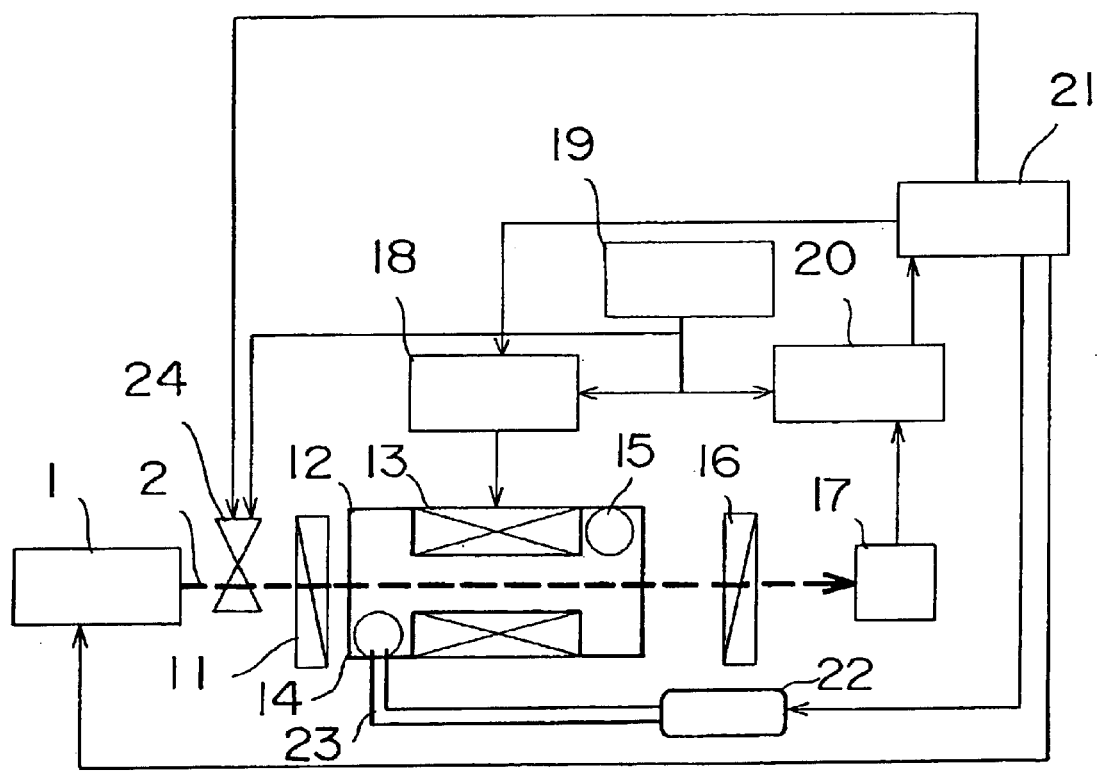
FIG. 14 is a schematic front view of a third example of an apparatus for measuring a concentration of solution in accordance with the present invention.

FIG. 14 is a schematic view of a measuring apparatus in accordance with this embodiment, which is obtained by adding a light modulator 24 to the apparatus of FIG. 13, in which reference numerals other than the light modulator 24 are identical with those of FIG. 13. The light modulator 24 performs intensity modulation on the substantially parallel light 2 at a modulation frequency of the signal generator 19 when supplied with directions from the computer 21. During the measurement of the optical rotation, modulation is not carried out based on the directions from the computer 21, so that the apparatus is fixed in a state in which the substantially parallel light 2 is completely transmitted therethrough.

In this embodiment, the optical rotation is measured in the same manner as in Embodiment 6. When the protein concentration is measured, a current is not passed through the solenoid coil 13, and the intensity modulation is carried out on the substantially parallel light 2 by the light modulator 24 under the directions from the computer 21. At this step, the lock-in-amplifier 20 also performs a phase sensitive detection on the output signal from the photosensor 17 using the output signal from the signal generator 19 as a reference signal. Since the output signal from the lock-in amplifier 20 substantially reflects the transmittance of the solution to be detected, the output signal from the lock-in amplifier 20 can be considered as the transmitted light intensity. Therefore, the computer 21 controls the pipette 22 to mix the sulfosalicylic acid reagent through the inlet port 14 into the sample cell 12, and analyzes the changes in output signal from the lock-in-amplifier 20 before and after the mixing, thereby making it possible to measure the protein concentration with precision. The concentration of the optical active substance other than the protein can be determined from the measured protein concentration and optical rotation in the same manner as in Embodiment 6.

Incidentally, either in this embodiment or Embodiment 6, the polarizer 11 is arranged with the analyzer 16 in a crossed nicols state, and hence the intensity of the light reaching the photosensor 17 is very low. Therefore, as in this embodiment, the substantially parallel light 2 is subjected to the intensity modulation, and the output signal from the photosensor 17 is subjected to the phase sensitive detection to restrict the band, thereby achieving the very high effect of improving the signal to noise ratio (S/N), and improved measurement precision of the protein concentration.

As described above, in accordance with this embodiment, the protein concentration can be measured with high precision by modulating the substantially parallel light 2. This embodiment exhibits a particularly high practical utility when the solution to be detected is a urine.

Further, in each of the foregoing embodiments of the present invention, there has been shown the configuration in which, when a reagent is mixed, the reagent is directly injected by a pipette or the like into the solution to be detected. However, the same effect can be obtained even with the configuration in which the reagent is added dropwise to the solution to be detected.

As described above, in accordance with the present invention, the influences of the turbidity and coloration inherent with the solution to be detected, the influence of the reduction in transmittance of the optical window, etc., and the like can be corrected to determine a precise concentration of the specific component such as protein. Further, the measurable concentration range of the solution to be detected can be enlarged.

As a result, the concentration of the specific component in the solution to be detected can be determined with a high precision. Moreover, it becomes possible to determine the solution concentration, especially the protein concentration in a urine with high reliability and high practical utility in a laborsaving manner.

Further, it is also possible to determine both the concentrations of the protein and the optical active substances other than the protein in the solution to be detected. Especially when the solution to be detected is a urine, since the urine protein concentration and the urine sugar value can be determined with precision at the same time, the urinalysis process can be largely simplified, and the practical effect thereof is very high.

Although the present invention has been described in terms of the presently preferred embodiments, it is to be understood that such disclosure is not to be interpreted as limiting. Various alterations and modifications will no doubt become apparent to those skilled in the art to which the present invention pertains,-after having read the above disclosure. Accordingly, it is intended that the appended claims be interpreted as covering all alterations and modifications as fall within the true spirit and scope of the invention.

What is claimed is:

1. A method for measuring a concentration of solution comprising the steps of:

measuring transmitted light intensities and scattered light intensities of a solution to be detected containing a specific component before and after mixing a reagent, which changes the optical characteristics of said solution to be detected attributed to said specific component; and determining the concentration of said specific component in said solution to be detected on the basis of these measured values, wherein the concentration of said specific component in said solution to be detected in a low concentration region is determined from the measured values of the scattered light intensities before and after the mixing of said reagent, and the concentration of said specific component in said solution to be detected in a high concentration region is determined from the measured values of the transmitted light intensities before and after the mixing of said reagent.

2. A method for measuring a concentration of solution comprising the steps of:

measuring transmitted light intensities and scattered light intensities of a solution to be detected containing a specific component before and after mixing a reagent, which changes the optical characteristics of said solution to be detected attributed to said specific component; and determining the concentration of said specific component in said solution to be detected on the basis of these measured values, wherein the measured values of the transmitted light intensities before and after the mixing of said reagent are compared with the measured values of the scattered light intensities before and after the mixing of said reagent, thereby to detect the occurrence or non-occurrence of a false measurement due to a particle suspending in said solution to be detected.

3. The method for measuring a concentration of solution in accordance with claim 1, wherein at least one of the transmitted light intensities and the scattered light intensities before and after the mixing of said reagent is measured under the same condition for a standard solution with a known concentration and said solution to be detected, and the measured values of said solution to be detected are corrected by the measured values of said standard solution to determine the concentration of said specific component in said solution to be detected.

4. The method for measuring a concentration of solution in accordance with claim 3, wherein said standard solution is water not containing said specific component.

5. A method for measuring a concentration of solution, comprising the steps of:

measuring transmitted light intensities and/or scattered light intensities of the solution to be detected containing a protein before and after mixing a reagent, which changes the optical characteristics of said solution to be detected attributed to said protein;

determining the concentration of said protein in said solution to be detected on the basis of these measured values;

determining a concentration of an optical active substance in said solution to be detected by measuring the optical rotation of said solution to be detected before the mixing of said reagent; and then determining the concentration of the optical active substance other than said protein from said protein concentration and said optical rotation.

6. A method for measuring a concentration of solution comprising the steps of:

measuring a transmitted light intensity and a scattered light intensity of a solution to be detected containing a specific component after mixing a reagent, which changes the optical characteristics of said solution to be detected attributed to said specific component; and determining the concentration of said specific component in said solution to be detected on the basis of these measured values, wherein the concentration of said specific component in said solution to be detected in a low concentration region is determined from the measured value of the scattered light intensity after the mixing of said reagent, and the concentration of said specific component in said solution to be detected in a high concentration region is determined from the measured value of the transmitted light intensity after the mixing of said reagent.

7. A method for measuring a concentration of solution comprising the steps of:

measuring a transmitted light intensity and a scattered light intensity of a solution to be detected containing a specific component after mixing a reagent, which changes the optical characteristics of said solution to be detected attributed to said specific component; and determining the concentration of said specific component in said solution to be detected on the basis of these measured values, wherein the measured value of the transmitted light intensity after the mixing of said reagent is compared with the measured value of the scattered light intensity after the mixing of said reagent, thereby to detect the occurrence or non-occurrence of a false measurement due to a particle suspending in said solution to be detected.

8. The method for measuring a concentration of solution in accordance with claim 6, wherein at least one of the transmitted light intensity and the scattered light intensity after the mixing of said reagent is measured under the same condition for a standard solution with a known concentration and said solution to be detected, and the measured values of said solution to be detected are corrected by the measured values of said standard solution to determine the concentration of said specific component in said solution to be detected.

9. A method for measuring a concentration of solution comprising the steps of:

measuring a transmitted light intensity and/or a scattered light intensity of a solution to be detected containing a protein after mixing a reagent, which changes the optical characteristics of said solution to be detected attributed to said protein;

determining the concentration of said protein in said solution to be detected on the basis of these measured values;

determining a concentration of an optical active substance in said solution to be detected by measuring the optical rotation of said solution to be detected before the mixing of said reagent; and then determining the concentration of the optical active substance other than said protein from said protein concentration and said optical rotation.

* * * * *